US007846447B2

(12) United States Patent
Horn et al.

(10) Patent No.: US 7,846,447 B2
(45) Date of Patent: Dec. 7, 2010

(54) IMMUNOTHERAPY OF EPITHELIAL TUMORS USING INTRALESIONAL INJECTION OF ANTIGENS THAT INDUCE A DELAYED TYPE HYPERSENSITIVITY REACTION

(75) Inventors: Thomas Dag Horn, Little Rock, AR (US); Sandra Marchese Johnson, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 12/077,508

(22) Filed: Mar. 19, 2008

(65) Prior Publication Data

US 2008/0193410 A1    Aug. 14, 2008

Related U.S. Application Data

(60) Continuation of application No. 10/081,185, filed on Feb. 25, 2002, now abandoned, which is a division of application No. 09/344,357, filed on Jun. 25, 1999, now Pat. No. 6,350,451.

(51) Int. Cl.
*A61K 39/00* (2006.01)
(52) U.S. Cl. .................. 424/184.1; 514/2; 424/85.4
(58) Field of Classification Search ........................ None
See application file for complete search history.

(56) References Cited

U.S. PATENT DOCUMENTS

| 5,662,903 | A | 9/1997 | Boyer et al. |
| 6,033,673 | A | 3/2000 | Clements |
| 6,123,948 | A | 9/2000 | Whittle et al. |
| 2002/0009429 | A1 | 1/2002 | Bostwick |

FOREIGN PATENT DOCUMENTS

WO    WO 95/13089    5/1995

OTHER PUBLICATIONS

Harada, S., The Japanese Journal of Dermatology (Nippon Hifuka Gakkai Zashi), 1979, vol. 89, pp. 397-402.*
Heisser et al., Delayed type hypersensitivity (DTH) skin testing (SKT) for the evaluation of cellular immunity: Normal responses for adult men and women, Jan. 1996, p. 399 , Program and Abstracts of Papers to be Presented during Scientific Sessions 52nd Annual Meeting Journal of Allergy and Clinical Immunology, vol. 97, Issue 1, Part, 3.*
Amer et al., "Therapeutic evaluation for intralesional injection of bleomyclin sulfate in 143 resistant warts," *J. Amer. Acad. Dermatol.*, 18(15):1313-6 (1988).
Baker et al., "Therapeutic Approaches to Papillomavirus Infections," *Infectious Diseases in Dermatology*, 15(2):331-340 (1997).
Bolin, *Equine Disease Quarterly*, vol. 7, No. 3 (Apr. 1999).
Brodell et al., "The Treatment of Palmar and Plantar Warts Using Natural Alpha Interferon and a Needless Injector," *Dermatol Surg.*, 21:213-218 (1995) ® Elsevier Science, Inc.
Grier et al., "Regression of Cutaneous Melanosarcoma Following Intralesionsl *Mycobacterium bovis* BCG Injection: A Case Report," *J. of American Animal Hospital Association*, 14:76-81 (1978).
Horn, Thomas, "Intradermal Skin Testing and Treatment with Candida and Mumps Antigens of Verruca Vulgaris", Dialog Abstract No. 121478 dated Jun. 25, 1998.
Johansson et al., "Dinitrochlorbenzene (DNCB) Treatment of Viral Warts," *Acta. Derm Venereol*, 64:529-533 (1984).
Johnson et al., "Warts: A Guide to Their Removal," *Consultant* 39(1):253-266 (1999).
Klein et al., "Equine sarcoid: BCG immunotherapy compared to cryosurgery in a prospective randomised clinical trial," *Cancer Immunol Immunother* 21:133-140 (1986)® Springer-Verlag.
Landow, Ken, "Nongenital warts, When is treatment warranted?," *Postgraduate Medicine*, 99(3):245-249 (1996).
Miller, et al., "Human Papillomavirus Infection: Treatment Options for Warts," *American Family Physician* 53(1):135-143 (1996).
Miller et al., Ophthalmic Surg., vol. 25, No. 8, abstract only (1994).
Mond et al., Abstract of WO 95/13089 (1995).
Naples, et al., "Verruca Vulgaris: Treatment with Natural Interferon Alfa Using a Needleless Injector," *Arch Dermatol*, 129:698-700 (1993).
Naylor et al., "Contact Immunotherapy of Resistant Warts," *J. Am Acad Dermatol*, 19:679-83 (1988).
Nelson, Nancy, "Cancer Vaccines, Disappointing in the Past, Show Promise," *J. of the National Cancer Institute*, 88(8):486-488 (1996).
Pfister et al., "Role of HPV in Cutaneous Premalignant and Malignant Tumors," *Clinics in Dermatology*, 15:335-347 (1997) ® Elsevier Science Inc., New York, New York.
Quan et al., "The role of human papillomavirus in carcinoma," *J. Am Acad Dermatol.*, 25(4):698-705 (1991).
Parsad et al., "Cimetidine and levamisole versus cimetidine alone for recalcitrant warts in children," *Pediatric Dermatology* (Jul.-Aug. 2001), vol. 18, No. 4, pp. 349-352, Abstract.

(Continued)

*Primary Examiner*—Misook Yu
(74) *Attorney, Agent, or Firm*—Hugh McTavish

(57) ABSTRACT

The pharmaceutical composition is useful for treating epithelial tumors in a subject and contains at least two antigens and a pharmaceutically acceptable carrier, where each of the antigens induces or is capable of inducing a cutaneous delayed type hypersensitivity (DTH) response in the subject. This composition is particularly useful in treating epithelial tumors, such as warts or verrucae, that are induced by or related to papillomavirus. Antigens useful in the present pharmaceutical composition are anergy panel antigens, such as killed mumps virus, candida extract, trichophyton extract or comparable antigenic extracts. An additional pharmaceutical composition, also useful for treating epithelial tumors, contains at least one antigen that induces or is capable of inducing a cutaneous DTH response in a subject, at least one cytokine or colony stimulating factor and a pharmaceutically acceptable carrier. Kits containing these pharmaceutical compositions are useful for this immunotherapy.

25 Claims, No Drawings

OTHER PUBLICATIONS

Aventis Pasteur, "Mumps Skin Test Antigen USP", Product Information Brochure as of Feb. 1997, 2 pages.
Bellone et al. (Immunology Today, v20 (10), 1999, pp. 457-462).
Gaiger et al. (Blood, vol. 96, No. 4, Aug. 2000, pp. 1480-1489).
Johnson et al., "Intralesional Injection of Mumps or *Candida* Skin Test Antigens; A Novel Immunotherapy for Warts," *Arch. Dermatol.* (Apr. 2001), vol. 137, pp. 451-455.
Phillips et al., "Treatment of Warts with *Candida* Antigen Injection," *Archives of Dermatology* (Oct. 2001), full paper, 7 pages.
Phillips et al., "Treatment of Warts with *Candida* Antigen Injection," *Arch. Dermatol.* (Oct. 2000), vol. 136, pp. 1274-1275, Vignette.
Signore, Letter commenting on "*Candida* Immunotherapy of Warts," *Arch. Dermatol.* (Sep. 2001), vol. 137, pp. 1250-1251.
Harada, "Clinical application of fungus extracts and their culture filtrates in the treatment of skin diseases: *Candida* vaccine in the treatment of warts," *The Japanese Journal of Dermatology* (*Nippon Hifuka Gakkai Zashi*) (1979), vol. 89, No. 6, pp. 397-402.
McConahy, "Common Warts: Immunity as a Result of Therapy," *CUTIS* (Feb. 1976), vol. 17, pp. 301-304.
Greensher, "The Treatment of Warts with Mumps Skin Test Antigen," *Society of Teachers of Family Medicine*, 9 pages.
Greensher, "Treatment of Laryngeal Papillomas with Mumps Skin Test Antigen," *The Lancet* (Oct. 25, 1980), pp. 920-921.
Naylor et al., "Contact immunotherapy of resistant warts," *Journal of the American Academy of Dermatology* (Oct. 1988), vol. 19, No. 4, pp. 679-683, Abstract.
Stedman's Medical Dictionary, 27th ed., 2000, Lippincott Williams, definition of "Antigen."
Janeway, C. et al., Immunobiology: The Immune System in Health and Disease, 3rd ed., 1997, Curr. Biol. Ltd., London, Chapter 11.
Nieuwenhuis, P. pp. 3-32 in The Physiology of Immunity, J.A. Marsh et al. eds., 1996, CRC Press, Boca Raton, FL.
Alberts, B. et al., Molecular Biology of the Cell, 1983, Garland Publishing, New York, pp. 951-1012.
Miller et al. 1994. The conjunctival wart: report of a case and review of treatment and options. *Ophthalmic Surg.* 25: 545-548.
Briggaman R A, Wheeler C E. Immunology of human warts. *J Am Acad Dermatol* 1979; 1:297-304.
Del Giudice, G, Pizza M, Rappuoli R. Molecular basis of vaccination. *Molecular Aspects of Medicine* 1998;19(1):1-70.
Phillips et al. 2000. Treatment of warts with *Candida* antigen injection. *Arch. Dermatol.* 136:1274-1275.
Signore. 2001 *Arch. Dermatol.* 137:1250-1251.
McConahy. 1976. Common warts: immunity as a result of therapy. CUTIS 17: 301-304.
Greensher, A. 1980. Treatment of laryngeal papillomas with mumps skin test antigen. *Lancet* (Oct. 25, 1980) pp. 920-921.
Johnson et al., 2001, Intralesional injection of mumps or *Candida* skin test antigens: a novel immunotherapy for warts. *Arch. Dermatol.* 137:451-455.
Morison, W. Cell-mediated immune responses in patients with warts. *Br J Dermatol* 1975; 93:553-556.
Benton, E C. Therapy of epithelial warts. *Clinics in Dermatology* 1997; 15:449-455.
Beutner, K R, Spruance S L, Hougham A J, Fox T L, Owens M L, Douglas J M. Treatment of genital warts with an immune-response modifier (imiquimod). *J Am Acad Dermatol* 1998; 38:230-9.
Amer, M, Diab N, Ramadan A, Galal A, Salem A. Therapeutic evaluation for intralesional injection of bleomycin sulfate in 143 resistant warts. *J Am Acad Dermatol* 1988; 18:1313-6.
Adler A, Safai B. Immunity in wart resolution. *J Am Acad Dermatol* 1979; 1:305-309.
Swinehart, J M, Skinner R B, McCarty J M, Miller B H, Tyring S K, Korey A, Orenberg E K. Development of intralesional therapy with fluorouracil/adrenaline injectable gel for management of condyloma acuminata: two phase II clinical studies. *Genitourin Med* 1997; 73:481-487.

Pfister H. Human papilomavirus and skin cancer. *Seminars in Cancer Biology*. 1992; 3(5):263-271.
Majewski, S, Jablonska S. Immunology of HPV infection and HPV associated tumors. *Int J Dermatol* 1998; 37:81-95.
Israel, R M. Treatment of warts by vaccination. *Arch Dermatol* 1969; 100:222-223.
Chan, L S, Vanderlugt C J, Hashimoto T, Nishikawa T, Zone J J, Black M M, Wojnarowska F, et al. Epitope Spreading: Lessons from autoimmune skin disease. *J Invest Dermatol* 1998; 110:103-109.
Malling, H J, Abreu-Nogueira J, Alvarez-Cuesta E, Bjorksten S, Bousquet J, Caillot D, Canonica G W, et al. Local immunotherapy. *Allergy* 1998; 53(10):933-44.
Shibata et al., 2001, Th1 adjuvant N-acetyl-D-glucosamine polymer up-regulates Th1 immunity but down-regulates Th2 immunity against a mycobacterial protein (MPB-59) in interleukin-l0-knockout and wild-type mice. *Infection and Immunity* 69:6123-6130.
Clifton, M, Johnson S, Roberson P, Kincannon J, Horn T. Immunotherapy for recalcitrant warts in children using intralesional mumps or *Candida* antigens. *Ped Dermatol* 2003; 20:268-271.
Scott, M, Nakagawa M, Moscicki A-B. Cell-mediated immune response to human papillomavirus infection. *Clin Diag Lab Immunol* 2001; 8:209-220.
Lichtenwalner et al., 2004, Heat shock protein 60 is the major antigen which stimulates delayed-type hypersensitivity reaction in the macaque model of *Chlamydia trachomatis salpingitis*. *Infection and Immunity*, 72:1159-1161.
Pinto, L A, Edwards J, Castle P E, et al. Cellular immune responses to human papillomavirus (HPV)-16 L1 in healthy volunteers immunized with recombinant HPV-16 L1 virus-like particles. *J Infect Des* 2003; 188:327-338.
Alexander, M, Salgaller ML, Celis E, Sette A, Barnes WA, Rosenberg SA, Stellar Stellar MA. Generation of tumor-specific cytolytic T lymphocytes from peripheral blood of cervical cancer patients by in vitro stimulation with synthetic human papillomavirus type 16 E7 epitope. *J Obstet Gynecol* 1996; 175:1586-1593.
Mittler, JN, Lee WT. Antigen-specific CD4 T cell clonal expansion and differentiation in the aged lymphoid microenvironment. I. The primary T cell response is unaffected. *Mech Ageing Dev* 2004; 125:47-57.
Horn, T D, Haskell J. The lymphocytic infiltrate in acute epithelial allogenic graft-versus-host reactions lacks evidence for phenotypic restriction in donor-derived cells. *J Cutan Pathology* 1998:210-214.
Tyring, S, Edwards L, Cherry L K, Ramsdell W M, Kotner S, Greenberg M D, Vance C, Barnum G, Dromgoole S H, Killey F P. Safety and efficacy of 0.5% podofilox gel in the treatment of anogenital warts. *Arch Dermatol* 1998; 134:33-38.
Malejczyk, J, Majewski S, Jablonska S. Cellular immunity in epithelial and genital HPV infections. *Clinics in Dermatology* 1997; 15:261-274.
Majewski, S, Jablonska S. Human papillomavirus-associated tumors of the skin and mucosa. *J Am Acad Dermatol* 1997; 36:659-85.
Zabawski, E J, Cockerell C J. Topical and intralesional cidofovir: a review of pharmaocolgy and therapeutic effects. *J Am Acad Dermatol* 1998; 39:741-45.
Feldman, S R, Fleisher A B, Williford P M, Jorizzo J L. Destructive procedures are the standard of care for treatment of actinic keratosis. *J Am Acad Dermatol* 1999; 40:43-7.
Edwards, L, Ferenczy A, Eron L, Baker D, Owens M L, Fox T L, Hougham A J, Schmitt K A, et al. Self-administered topical 5% imiquimod cream for external anogenital warts. *Arch Dermatol* 1998; 134:25-30.
Fulginiti, MDVA and MDJH Arthur, 1969, Altered reactivity to measles virus: skin test reactivity and antibody response to measles virus antigens in recipients of killed measles virus vaccine. *J. Pediatrics* 75:609, abstract only.
M-M-RII. http://www.rxlist.com/m-m-r-ii-drug.htm. Accessed Oct. 15, 2009.

* cited by examiner

IMMUNOTHERAPY OF EPITHELIAL TUMORS USING INTRALESIONAL INJECTION OF ANTIGENS THAT INDUCE A DELAYED TYPE HYPERSENSITIVITY REACTION

CROSS-REFERENCE TO RELATED PATENT APPLICATIONS

This application is continuation application under 35 U.S.C. §120 of application Ser. No. 10/081,185, filed Feb. 25, 2002 now abandoned, which is a divisional of application Ser. No. 09/344,357, filed Jun. 25, 1999, now U.S. Pat. No. 6,350, 451. This application claims only subject matter disclosed in the parent applications and therefore presents no new matter.

STATEMENT AS TO THE RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

Field of the Invention

The present invention relates to immunotherapy of epithelial tumors, particularly tumors that are induced by infectious agents, particularly viruses, and particularly papilloma viruses. The immunotherapy of the present invention relates to the intralesional injection of at least one antigen into a epithelial tumor of a subject in need of treatment, wherein the subject to be injected had previously developed a naturally-occurring delayed type hypersensitivity (DTH) response to the antigen. The immunotherapy of the present invention is particularly useful for treating verrucae, condyloma, cervical carcinoma and bowenoid papulosis.

Verrucae or human warts are benign epidermal tumors caused by human papilloma virus (HPV). HPV is a member of the papovavirus family. HPV is a non-enveloped double-stranded deoxyribonucleic acid (DNA) virus that replicates in epithelial cells. This means that HPV has a predilection for the mucosa and skin. Currently, there are more than 70 distinct HPV types recognized each with at least a 10% genome difference. Because papillomaviruses tend to be host-specific and HPV has not been successfully grown in culture; the majority of the research with papilloma virus has been conducted with animal papillomaviruses. (37) Papillomaviruses are considered responsible for several forms of viral infection ranging from relatively benign warts of the skin or mucous membranes to cancer, the most significant being cervical cancer. Papillomaviruses are known to infect mammals, including humans, rabbits, canines, felines, bovines and equines. Papillomaviruses are highly species and tissue-specific, and are characterized by a specific mode of interaction with the squamous epithelia they infect. These viridae colonize various stratified epithelia like skin and oral and genital mucosae, and induce the formation of self-limited benign tumors, known as warts or condylomas.

Verrucae are transmitted usually by direct human-to-human transmission with a variable incubation period and clinical presentation. Symptomatic disease includes flat warts (verruca plana), common warts (verruca vulgaris), filiform warts, palmar and plantar warts, condyloma acuminata (venereal warts), myrmecia, focal epithelial hyperplasia, epidermodysplasia verruciformis, laryngeal warts, cervical cancer and anogenital cancer. (1) Warts in and of themselves cause significant morbidity and warrant aggressive therapy.

Verrucae have reached epidemic or even pandemic proportions. In 1990, there was an estimated 79% lifetime risk of acquiring HPV with an annual incidence of 8%. (1) Decreasing the burden of visible wart in a community would be expected to decrease infectivity and help stem the epidemic. Aside from the clinical dermatological burden that HPV causes in our society, it is well known that there is an oncogenic burden caused by HPV. HPV is thought to play a causative role in the formation of cervical carcinoma and anogenital carcinoma in immunocompetent hosts. (27, 29-31, 37, 39) HPV is known to be important in the pathogenesis of carcinomas (squamous cell carcinoma mainly) of immunosuppressed individuals, such as those who are iatrogenically immunosuppressed, infected with the human immunodeficiency virus, affected with epidermodysplasia verruciformis, and after organ transplant. (27, 29-31, 39) Given this knowledge and the expectation of inducing systemic immunity to HPV by epitope unveiling utilizing antigens that have induced a DTH response in the subject to be treated, this novel immunotherapy provides a potential therapy for HPV induced malignant neoplasms.

In renal transplant patients with actinic keratoses and squamous cell carcinoma, there is evidence that the epithelial tumors are HPV-induced. Also, there is a clear association between cervical carcinoma and HPV infection. The application of DTH reactions to various antigens in the treatment of in-situ, invasive and metastatic cervical carcinoma may provide clinical benefit to the extent that the tumor cells express epitopes of the HPV. It follows that other, non-HPV-related neoplasms can also be treated similarly in that elicitation of a brisk immune response in the tumor may result in recognition of a tumor-associated antigen resulting in tumor-directed immunologic response.

With the exception of flat warts that have a fine almost imperceptible roughness on the surface, warts show finger-like projections or rough papular projections and scaling which correspond to the papillomatosis noted histopathologically. The verrucous surface is an important diagnostic feature of warts. Since dilated dermal blood vessels are present within the projections, warts commonly bleed when irritated. The diagnosis is usually made clinically but the diagnosis can be confirmed with biopsy, polymerase chain reaction, or in-situ hybridization.

HPV infection clearly is associated with cancer. Squamous cell carcinoma has been shown to contain HPV-16. (1) Dysplastic periungual papillomas have been shown to have HPV-57. Epidermodysplasia verruciformis is a genetic condition of altered cell-mediated immunity in which affected individuals develop chronic HPV infection and squamous cell carcinoma. There are other states of immunosuppression, both congenital and acquired, that lend to heightened HPV infection and HPV-associated malignancies. (3) The risk of malignant transformation may or may not be decreased with treatment. (1) At a minimum, treatment to decrease the spread of HPV may prevent others from developing a cancer promoting infection. (3)

Finally, small warts are easier to treat than large warts. The best study of the natural history of warts suggests that only 40% of patients with warts would have all of their warts disappear without treatment after two years. (8) Therefore, it is more likely than not that over several years, warts will continue to enlarge, spread, and become more resistant to treatment. Better to destroy clinically visible warts when they are small and immediately treat any recurrent lesions than to wait and see which will disappear and which will pose more serious treatment problems.

There is no perfect treatment for warts. An antiviral wart antibiotic or vaccine is being researched but does not exist for treatment today. Currently, there are destructive, immunomodulative, chemotherapeutic and other modalities used to treat HPV-associated tumors. (5)

Patients often present to the doctor with a wart after they have suffered with it for some time. They frequently have tried over-the-counter and herbal remedies. The mechanism of action of all of the currently available therapies is either destruction (e.g., cryotherapy), chemotherapeutic (e.g., bleomycin) or immunomodulation (e.g., interferon) in nature. There is a multitude of therapies currently available for the treatment of HPV infection. The following is a list of the most widely employed wart therapies: Liquid nitrogen, Cantharidin (a blistering agent derived from Spanish fly extract), surgical excision, Carbon Dioxide ($CO_2$) Laser Ablation, Vascular Lesion Laser, electrosurgery, bleomycin, glutaraldehyde, formaldehyde, podophyllin, topical retinoic acid, Interferon-α (IFN-α), Imiqimod (a non-nucleoside heterocyclic amine that is a potent inducer of IFN α in humans), Dinitrochlobenzene (DNCB), Diphencypropenone (DPCP), radiation therapy, ultrasound, hypnosis, and acupuncture. (1-57) There is a 12% to 56% failure rate with podophyllotoxin used for condyloma and a 50% failure rate of external genital warts with IFN-α plus cryotherapy. (1) The rate of recurrence of common warts after surgical excision is 15-30%, after laser ablation is 5-10% and after liquid nitrogen is 39%. (1, 2) The high reported rates of recurrence (the true recurrence may even be higher) may be due to inherent or functional lack of immunity to HPV by the patient.

Recognizing the effectiveness of cryotherapy, there remains a pressing need for additional therapies in the treatment of verrrucae. Liquid nitrogen exerts its effects by epidermal and dermal cellular destruction. The effectiveness of cryotherapy is operator dependent. The duration of the freeze-thaw cycle is important since too little liquid nitrogen provides minimal effect whereas too much liquid nitrogen results in adverse effects. The expected adverse effects include scar, pain, burning, edema and possibly ulceration. (23) Many warts are too large for comfortable use of cryotherapy.

Human interferon-α is known to be useful in the treatment of several viral infections, including chronic hepatitis B virus and herpes zoster. U.S. Pat. No. 5,165,921 discloses treating condyloma acuminatum, commonly referred to as genital warts, known as benign, fibro-epithelial tumors associated with various papilloma viruses, with a topical formulation of interferon-α. Additionally, warts can also be treated by direct injection of interferon into the warts. (16, 17) Immunotherapy using an unrelated agent to cause an immune response is certainly not a new idea. This technique has proven successful for the treatment of melanoma, multiple myeloma, chronic myeloid leukemia, and bladder carcinoma. (62-66)

Immunotherapy in the treatment of warts has been attempted in the past with trials of sensitization to dinitrochlorbenzene (DNCB) and other chemicals. DNCB is now known to be mutagenic in the Ames assay and therefore rarely used. This immunotherapy approach is also problematic. Sensitization must first be attempted (often unsuccessfully) in order to develop a brisk immune response upon topical application of DNCB to the wart. In contrast to the topical application of DNCB, the immunotherapy of the present invention injects the antigen directly into the wart or tumor, thus evoking a stronger immune response.

SUMMARY OF THE INVENTION

Thus, a need exists for an epithelial tumor therapy that provides successful and long lasting results. The present invention is based upon the discovery that successful resolution of epithelial tumors requires a specific immunologic response to the causative agent of the epithelial tumors. The present invention is based upon the discovery that standard antigens currently employed in anergy panels with a high prevalence of reactivity in human and other mammals result in the elicitation of a DTH response. This response which at first glance appears to be non-specific for the causative agent of the epithelial tumor, in fact, results in a very specific response when the standard antigen to which the subject has previously reacted, is directly injected into the epithelial tumor. The results of the studies show that the present immunotherapy offers significant and long lasting cure rates directly related to the induction or stimulation of existing immunity as compared to cryotherapy. The present method takes advantage of this prior sensitization to an unrelated infectious agent through intralesional injection to evoke a strong secondary immune response against the causative agent of the epithelial tumor, such as the papillomavirus. The data obtained from studies support that the present immunotherapy method results in a significant number of patients achieving complete resolution of warts. Additionally, some patients receiving the present immunotherapy to a specific wart or tumor have experienced resolution of untreated warts at sites distant from the site of injection, which suggests that the present immunotherapy induces or stimulates existing papillomavirus specific immunity. This resolution took place slowly and in a timeframe associated with the injection of the primary verruca. One can conclude that specific immunity to the causative agent of the tumor was stimulated or induced by the immunotherapy of the primary wart which resulted in a systemic response targeting the causative agent, such as HPV for example, throughout the skin. This observation heightens the potential therapeutic value of the immunotherapy protocol for treating epithelial tumors, as well as for other causative agents of associated conditions. Papillomavirus-specific immunity is an example of such a causative agent.

The proposed hypothesized mechanism of action of intralesional injection of an antigen is unveiling of the HPV antigen and epitope spreading. (60) This action will lead to a generalized systemic immune response to HPV and might lead to resolution of all present and future clinical tumors caused by HPV.

The present immunotherapy includes diagnosing the subject having epithelial tumors or skin derived tumors, such as melanoma, then testing the subject with antigens from an anergy panel by injecting intradermally small amounts of anergy panel antigens, such as killed mumps virus protein extract, candida extract, trichophyton extract or comparable antigenic extracts, and determining the reaction of the subject to the antigens. The antigen that elicits the strongest cutaneous DTH response in the subject is selected and injected directly into the epithelial tumor over a period of time at designated intervals until the tumor resolves.

In one embodiment, the present invention relates to a method of treating epithelial tumors or skin derived tumors, such as melanoma, comprising injecting an effective amount of a pharmaceutical composition containing at least one antigen into the tumor, wherein the antigen induces or is capable of inducing an cutaneous DTH response in the subject prior to the injection of the antigen into the tumor. This immunotherapy is particularly useful in treating epithelial tumors, such as cutaneous tumors, including warts or verrucae, that are induced by or related to papillomavirus.

In a further embodiment, the invention relates to a method of treating epithelial tumors comprising injecting the tumors with at least one antigen and at least one additional one cytokine or colony stimulating factor. The antigen and cytokine or colony stimulating factor may be in the same pharmaceutical composition, thereby injected simultaneously, or may be in two different pharmaceutical compositions and injected sequentially. The cytokine may be interferon-$\alpha$, interferon-$\beta$, interferon-$\gamma$, interleukin-2 or interleukin-12. The colony stimulating factor may be granulocyte-macrophage colony stimulating factor. The subject treated by the present immunotherapy is preferably a mammal selected from a human, rabbit, canine, feline, bovine, equine or ovine subject but also could be avian.

In another embodiment, the invention relates to a pharmaceutical composition for treating epithelial tumors comprising at least two antigens, each of which induces or is capable of inducing an cutaneous DTH response in the subject prior to the injection of the antigens into the tumor, and a pharmaceutically acceptable carrier formulated for injection into an epithelial tumor. This pharmaceutical composition may further comprise a cytokine or a colony stimulating factor.

In another embodiment, the invention relates to a syringe and needle suitable for use in injecting the above described pharmaceutical compositions into an epithelial tumor, wherein the pharmaceutical composition is stored within the syringe. In another embodiment, the invention relates to a kit comprising a syringe and needle suitable for injecting the above described pharmaceutical compositions into an epithelial tumor. The kit further comprises one or more containers containing the above described antigens and/or a cytokine or colony stimulating factor.

DETAILED DESCRIPTION OF THE PREFERRED EMBODIMENT

In one embodiment, the present invention relates to a method of treating epithelial tumors comprising injecting an effective amount of a pharmaceutical composition comprising at least one antigen into the tumor, wherein the antigen induces or is capable of inducing a cutaneous DTH response in the subject prior to the injection of the antigen into the tumors. The epithelial tumor can be induced by a virus, preferably a papillomavirus, and more preferably by a human papillomavirus. Papillomaviruses of other species of mammals can induce epithelial tumors in dogs, cows, horses and other species susceptible to papillomaviruses, such as birds.

The method of the present invention is directed to treating an epithelial tumor in a subject. This tumor can include both benign and malignant tumors. Preferably, the tumor is a verruca (wart), a condyloma (a genital wart), a cervical carcinoma, bowenoid papulosis, a laryngeal papilloma or epidermodysplasia verruciformis but can also include skin derived tumors, such as melanomas. The verruca to be treated can be of a number of subtypes, such as verruca vulgaris, verruca plantaris, verruca palmaris or verruca plana.

The antigen that is injected into the epithelial tumor is selected for its ability to induce a cutaneous DTH response in a subject. There is no currently available compound which is known to unveil HPV and procure an HPV specific systemic immune response. Injection of cytokines, such as interferon upregulates the immune responses to HPV but does not cause a cutaneous DTH response and interferon is not an antigen. The present invention is not intended to cover the direct injection of interferon into the tumor without either simultaneous or sequential injection of an antigen. Thus, one aspect of the present invention is directed to simultaneous or sequential injection of the antigen and a cytokine or CSF into the tumor. Injection of bleomycin inhibits DNA synthesis. Topical application of DNCB or other contact sensitizers acts by elicitation of contact hypersensitivity at the site of administration. All of these act in a nonspecific manner and do not lead to resolution of distant warts. Intralesional injection of an antigen into one epithelial tumor has been demonstrated to lead to resolution of distant epithelial tumors.

The induction of the DTH response in the subject is tested by intradermally injecting small amounts of anergy panel antigens and determining the reaction of the subject to the antigens. The antigen that elicits the strongest response in the subject is selected and injected directly into the epithelial tumor over a period of time at designated intervals until the tumor resolves. If more than one antigen gives a strong response measured by an area of induration of at least 5 mm in diameter, then more than one antigen can be selected for injection into the epithelial tumor.

The antigen is an antigenic determinant of the antigen, a hapten or an epitope that is responsible for inducing the cutaneous DTH response in the subject. The antigen is preferably a biological substance but it can be a chemical substance if the chemical is not carcinogenic or mutagenic as measured by the Ames test or any other art recognized assay that identifies substances as carcinogenic or mutagenic. It is important that no antigens categorized as carcinogenic or mutagenic be injected into the tumors treated by the present method. The antigens useful in the present invention can be of viral, fungal or bacterial origin. It is preferred that the antigens useful in the present invention are derived from naturally occurring infectious agents to which the majority of the subjects of the treated species have naturally acquired immunities or to which the subject to be treated has been immunized against. In other words, the preferred antigens to use are those viral, fungal and bacterial antigens to which most healthy subjects are already currently sensitized. A positive skin test denotes prior antigenic exposure and DTH immunity. Injection of the antigen into the epithelial tumor or skin derived tumor will therefore lead to an immune response that is composed of various known and unknown immune modulators. The immune response may consist of white blood cells including lymphocytes and Langerhans cells as well as the cytokines they secrete. These cytokines are not limited to interferon-$\alpha$. They include other immune modulators such as other interferons, interleukins, leukoreglins, and growth factors. Therefore, the immune response from injection of an antigen is much greater than that elicited by injection of interferon-$\alpha$.

Such preferred antigens for treating humans are allergenic extracts for intradermal testing available from a number of different companies, such as Bayer Corporation, Elkhart, Ind. 46515 or as a skin test antigen, such as Mumps Skin Test Antigen USP available from Pasteur Merieux Connaught, Swiftwater, Pa. 18370. Preferred antigens useful to inject into a human epithelial tumor are mumps skin test antigen, candida extract and trichophyton extract, all of which are prepared in combination with a pharmaceutically acceptable carrier, such as isotonic saline and which are known to persons skilled in the art. A preferred candida extract is the *Candida albicans* Skin Test Antigen available from known commercial sources. The antigens used for injection into the epithelial tumor are preferably not composed of live agents but instead are preferably composed of killed or parts of agents, thus reducing the risk of contracting a disease caused by the live agents.

The present method of treating a epithelial tumor optionally can include injecting at least one additional pharmaceutical composition containing at least one cytokine or colony stimulating factor (CSF) into the tumor. This optional injection can occur simultaneously with or after the injection of the antigen. The CSF preferably is granulocyte macrophage colony stimulating factor, such as Leukine® (sargramostim), which is a recombinant human granulocyte macrophage colony stimulating factor (GM-CSF) in a injectable pharmaceutically acceptable carrier obtained from Immunex Corporation, Seattle, Wash. 98101. The GM-CSF boosts the number and function of the Langerhans cells in the epidermis and possibly the dermis. The Langerhans cells present antigen to naive and memory cells, thus promoting Langerhans cell function which in turn boosts the DTH response. Any of the cytokines, such as interferon-α, interferon-β, interferon-γ, interleukin-2 or interleukin-12 can be utilized to enhance the treatment of the epithelial tumor. Preferred interferons, such as interferon-α 2a, interferon-α 2b, and interferon-α N3, interferon-β 1a and interferon-β 1b and interferon-γ in pharmaceutically acceptable carriers are useful in the present method. Roferon®-A is an example of an acceptable recombinant interferon-α-2a that is commercially available and useful in the present invention and which is obtained from Roche Laboratories, Nutley, N.J. 07110.

The method of the invention can utilize any device that injects the antigen into the epithelial tumor so that the injected solution enters at least the epidermis or the dermis of said subject. Particularly useful in the present method is a hypodermic needle or high pressure injection device sufficient for the antigen(s) to enter at least the epidermis or dermis of said subject. These devices and modes of injection can be used to deliver the antigen as well as the cytokine or colony stimulating factor to the epithelial tumor.

Thus, in one embodiment, the invention relates to a pharmaceutical composition comprising at least two of the above described antigens and a pharmaceutically acceptable carrier that has been formulated for injection into an epithelial tumor. Injecting at least two antigens increases the likelihood that the composition will induce a DTH response in the subject. The pharmaceutical composition may contain preservatives and other non-immunogenic additives, according to methods well known in the art. See, e.g. Remington's Pharmaceutical Sciences: Drug Receptors And Receptor Theory, (18th ed.), Mack Publishing Co., Easton, Pa. (1990). In another embodiment, such pharmaceutical composition may also contain one or more cytokines or colony stimulating factors, as described above.

In yet another embodiment, the invention relates to a syringe containing any of the above described pharmaceutical compositions, wherein such pharmaceutical compositions are stored in such syringe and wherein the syringe can be used for injecting the pharmaceutical compositions into an epithelial tumor. In another embodiment, the invention is directed to a kit which comprises one or more containers containing the above described antigens and/or cytokines. Such kit may also contain a syringe and needle suitable for injecting the antigens into an epithelial tumors. The kit may also contain appropriate instructions for use.

Preferably, the present method and pharmaceuticals treat a mammal. More preferably, a human is treated but the present method is useful for treating any mammal that is afflicted by epithelial tumors. Such other non-human mammals are dogs, cats, rabbits, cows or cattle, horses and sheep. Any non-human mammal that is susceptible to and contracts papillomavirus induced epithelial tumors are subject that can be treated by the present method, such as birds.

In its preferred embodiment of treating humans having HPV-induced epithelial tumors or melanomas, the method of the present invention takes advantage of the prior sensitization to candida and mumps prevalent in the population. Candida and mumps were chosen over other antigens because they are FDA approved traditional DTH controls utilized for anergy testing. Additionally, persons skilled in the art also are familiar with the local induration and erythema that is expected with intradermal injection of these antigens. There are other antigens available for DTH testing, such as trichophyton, but that are not FDA approved for intradermal injection at this time that also would be appropriate for use in the present invention.

The present invention provides for both a prognostic instrument to predict response to standard therapy and to develop a novel treatment option for epithelial tumors, such as verrucae. Verrucae are often recalcitrant to multiple treatment modalities including liquid nitrogen, bleomycin, cantharidin, and podophyllin. Topical immunotherapy with dinitrochlorobenzene is known to be effective by elicitation of contact dermatitis. The present approach to immunotherapy utilizes standard antigens currently employed in anergy panels with a high prevalence of reactivity in humans and elicitations of a DTH response are utilized in our method. Furthermore, since untreated warts resolve with the present approach, elicitation of HPV-specific immunity should provide less relapse and longer remissions.

Example

The following description is the protocol for identifying the antigens to be used in the claimed method. After the diagnosis of epithelial tumors, such as verruca, such as is made in the subject, small amounts of antigens, such as mumps and candida, are separately injected intradermally on the surface of the skin, e.g., the volar forearm of a human subject. If the subject reacts to the antigen(s), intralesional injection with the antigen that elicited the greater response is utilized.

While verrucae may respond to destructive mechanisms such as cryotherapy or laser ablation, complete resolution ultimately requires an HPV-directed immunologic response. The present immunotherapy will result in significant and long lasting cure rates directly referable to the induction or stimulation of existing HPV-specific immunity. The support for this hypothesis resides in two preliminary observations. First, a significant number of subjects achieved complete resolution of warts by the present immunotherapy. Second, some subjects receiving immunotherapy to a specific wart in the setting of multiple warts experienced resolution of untreated warts at distant sites.

Pilot Clinical Trial:

The following pilot clinical trial was carried out to determine the efficacy of the method and compositions of the present invention. The diagnosis of a wart was made by clinical examination of one or multiple well-circumscribed, hypertrophic papillary tumors. (6) At least one hundred fifty volunteers between the ages of 3 years old and 85 years old are to be evaluated. To be included in the study, the subject must have been willing to comply with all of the requirements of the protocol, had the capacity to understand and provide detailed informed consent prior to enrollment, and been able to return to the evaluation site for all necessary visits. A subject was excluded with a history of Gell-Coombs type I allergy to mumps or candida antigens or have any condition or compliance issue which in the opinion of the investigators might interfere with adequate evaluation or safety, such as pregnancy, infection with the human immunodeficiency virus-1, iatrogenic immunosuppression, primary immunodeficiency, or generalized dermatitis.

Once diagnosed, an anergy panel was placed: 0.1 milliliter of 40 cfu/ml was injected of Connaught manufactured Mumps Skin Test Antigen USP into the intradermal aspect of the left flexor forearm and 0.1 milliliter of Alcon candida antigen was injected intradermally into the right flexor forearm. DTH reactivity was determined 48 hours after intradermal placement by measuring the induration, not the erythema, in millimeters. A reaction was considered positive for either antigen if induration extended at least 5 mm in diameter around the injection site. A reaction was considered negative if the area of induration was less than 5 mm. If there was a lack of DTH response to both antigens, then conventional treatment with cryotherapy was initiated. This treatment consisted of paring every hyperkeratotic wart followed by two freeze-thaw cycles of liquid nitrogen ($LN_2$) for thirty seconds, each every three to six weeks until clinical clearance of the wart was obtained or for a total of ten treatments. If a positive DTH response to one or more antigens was elicited, the subject was randomized either to have conventional cryotherapy as above or therapy with the antigen that elicited the greater response. Randomization occurred according to order of acceptance into the study. That is, the first and subsequent odd numbered subjects received immunotherapy and the second and subsequent even numbered subjects received cryotherapy. Immunotherapy consisted of a titrated amount of the antigen that elicited the greater test response injected intralesionally and into the underlying dermis of only one, preferably the largest, wart. If the DTH response measured by induration was 5 mm to 20 mm then 0.3 mL of the antigen was injected. If the DTH response was 20 mm to 40 mm then 0.2 mL was injected. If the DTH response was greater than 40 mm then 0.1 mL was injected. Evaluation of the clinical response occurred in three week intervals.

The response was considered complete when there was disappearance of the warts and return of the normal skin markings. The response was considered partial if the warts regressed in size. If there was no decrease in size, then no clinical response was deemed to have occurred. If there is no clinical response or a clinical response of less than 25% by visual examination after 10 treatments or 30 weeks then the study was concluded for that subject. However, if immunotherapy failed to show any sign of resolution of the verruca vulgaris (VV) lesion after three injections, immunotherapy was discontinued and cryotherapy initiated. Telephone follow-up will occurred four months after the subject was considered free of warts.

The following Table A provides a flowchart of the protocol.

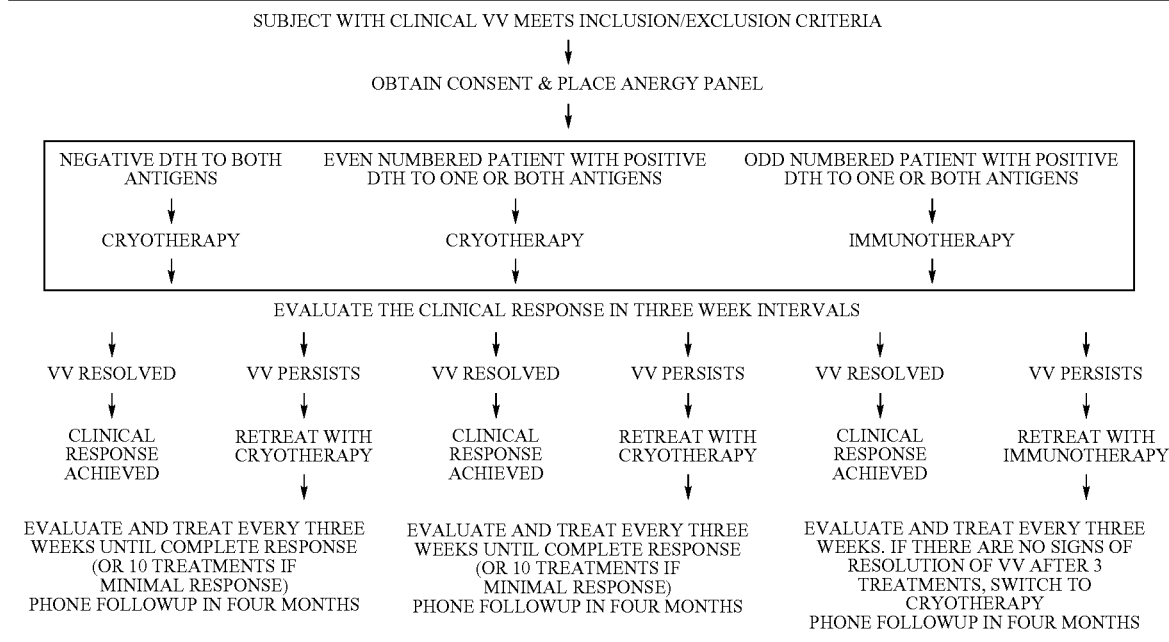

TABLE A: PROTOCOL FLOWCHART

The data collected in this therapeutic arm of the trial was primarily descriptive in nature. The safety, tolerability, and technical feasibility of this novel technique was confirmed. Each subject was assigned a unique number and a chart. All of the charts were stored in a labeled folder that was stored at the physician workstation to ensure subject confidentiality. Comparative statistical analysis allowed the investigators to determine if there was a significant advantage to intradermal skin testing and treatment with candida and mumps antigens.

The summary of accumulated data is provided in Table B. A chi-square analysis or comparison of two proportions will be used assuming a 15% difference in cure rates, alpha of 0.05, and power of 80% this will require 150 subjects to be included in the study.

Lymphocyte Proliferation Assay:

Twenty subjects were included in a concomitant arm of the study to investigate systemic response to relevant antigens in those subjects receiving immunotherapy. This investigation included obtaining 20 milliliters of blood at the initial visit and after two injections with the antigens. Using standard techniques, these samples were examined after Ficoll separation of mononuclear cells to look for a statistically significant increase in T cell proliferation as measured by thymidine incorporation in response to mumps, candida and HPV epitopes.[61]

The data collected in the lymphocyte proliferation assay was analyzed quantitatively for statistically significant differences in T cell proliferative responses referable to immunotherapy.

Histologic Evaluation:

Biopsies were taken of a regressing wart to view the histologic changes. Immunoperoxidase was performed utilizing standard techniques. (58, 59) Markers to Langerhans cells (CD1a), T cells (CD3), T helper/inducer cells (CD4), T cytotoxic/suppressor cells (CD8), B cells (CD20), interleukin 2 receptors (CD 25), and natural killer cells (CD56) were performed.

The data collected was descriptive in nature. The information demonstrated the nature and relative proportion of inflammatory cell infiltrate subsets.

TABLE B

|  | DTH NEG, CRYOTHERAPY | DTH POS, CRYOTHERAPY | DTH POS, IMMUNOTHERAPY |
|---|---|---|---|
| NO RESPONSE | 6 | 1 | 3 |
| PARTIAL RESPONSE | 0 | 0 | 2 |
| COMPLETE RESOLUTION | 4 | 6 | 13 |
| TOTAL NUMBER | 10 | 7 | 18 |
| % COMPLETE RESOLUTION | 40% | 85% | 72% |

|  | ALL CRYOTHERAPY | ALL IMMUNOTHERAPY |
|---|---|---|
| % COMPLETE RESOLUTION | 58% | 72% |

The general utilization of immunotherapy with antigens is outlined:

1. Make the diagnosis of an epithelial tumor or a melanoma, such as a papillomavirus induced tumor.
2. Do not include subjects with known sensitivity to eggs, thimerasol or the antigens.
3. Place 0.1 mL of at least one antigen intradermally into volar forearm.
4. Examine volar forearm in 48 to 72 hours to determine if there is an adequate cutaneous DTH response. DTH response is considered adequate if there is induration of at least 5 mm.
5. Inject antigen(s) with or without added immune modifiers, such as cytokines or CSFs, into the largest tumor based on the following titration: If DTH reaction is 5 mm to 20 mm then inject 0.3 ml of the antigen. If the DTH response was 20 mm to 40 mm, then inject 0.2 mL. If the DTH response was greater, than 40 mm then inject 0.1 mL. If cytokines, such as interferon, are also injected simultaneously with or sequentially to injection of the antigen, inject a dosage of between 250,000 to 1,000,000 I.U.s (International Units). If CSFs, such as GM-CSF, are also injected simultaneously with or sequentially to injection of the antigen, inject a dosage of between 250 mcg to 500 mcg.
6. Reassess clinical response every three weeks until tumor(s) is resolved. If tumor is still present, then reinject the largest tumor using the injection guidelines above. However, the amount and/or concentration of the antigen may be altered depending upon the reaction of the subject to the injected antigen. A strong reaction may require the same or lower concentration and a weak reaction may require increasing the concentration of the antigen. If there is no clinical response after 3 injections, consider altering the therapy.

Modifications of Immunotherapy Method

Step 3 of the immunotherapy described above may be modified by intradermally injecting more than one antigen. Such a modification would remove the need to inject a number of the antigens separately. The goal of step 3 is to determine one or more antigens that induce a cutaneous DTH response in the subject, and in most cases, it is not necessary to know the specific antigen from a mixture of antigens that causes the cutaneous DTH response as long as the mixture is injected into the tumor.

Step 5 of the immunotherapy described above may be modified by injecting more than one antigen into the tumor. The concentrations and amounts of the antigen may be varied as can be determined by the skilled artisan, a dermatologist. For example, if 0.2 mL of one antigen would be indicated for injection depending upon the cutaneous DTH response, then 0.1 mL of each of two antigens may be used. This dosage would ensure that the absolute concentration of the antigens injected remain approximately the same. The size of the tumor limits the amount (liquid volume) of antigen(s) that can be injected into the tumor. It may be necessary to concentrate the antigen so that a similar dosage is present in a smaller volume. It is well within the skill of the artisan to determine modifications to this immunotherapy using the guidelines of step 5 for injection into the tumor.

All citations to publications, books, patents, patent applications set forth herein are incorporated by reference in pertinent part or in its entirety.

CITATIONS

1. Baker G E, Tyring S K. Therapeutic approaches to papillomavirus infections. Dermatologic Clinics 1997; 15(2): 331-340.
2. Landow K. Nongenital warts: When is treatment warranted? Postgrad Med 1996; 99(3):245-249.
3. Johnson S M, Brodell R T. Treating warts: a review of therapeutic options. Consultant. 1999; 39(1):253-266.
4. Messing A M, Epstein W L. Natural history of warts: A two-year study. Arch Dermatol 1963; 87:306-10.
5. Miller D M, Brodell R T. Human papillomavirus infection: Treatment options for warts. Am Fam Phys 1996; 53(1): 135-43.
6. Kimble-Haas S. Primary care treatment approach to nongenital verruca. Nurse Practitioner 1996; 21(10):29-34.
7. Briggaman R A, Wheeler C E. Immunology of human warts. J Am Acad Dermatol 1979; 1:297-304.
8. Adler A, Safai B. Immunity in wart resolution. J Am Acad Dermatol 1979; 1:305-309.
9. Morison W. Cell-mediated immune responses in patients with warts. Br J Dermatol 1975; 93:553-556.
10. Benton E C. Therapy of epithelial warts. Clinics in Dermatology 1997; 15:449-455.
11. Sloan K, Haberman H, Lynde C W. Carbon dioxide laser-treatment of resistant verrucae vulgaris: retrospective analysis. J Epithelial Med Surg 1998; 2(3):142-5.

12. Beutner K R, Spruance S L, Hougham A J, Fox T L, Owens M L, Douglas J M. Treatment of genital warts with an immune-response modifier (imiquimod). J Am Acad Dermatol 1998; 38:230-9.
13. Bykowski M. Using intralesional bleomycin on tough warts. Skin & Allergy News July 1998:17.
14. Epstein E. Persisting Raynaud's phenomenon following intralesional bleomycin treatment of finger warts. J Am Acad Dermatol 1985; 13(3):468-71.
15. Amer M, Diab N, Ramadan A, Galal A, Salem A. Therapeutic evaluation for intralesional injection of bleomycin sulfate in 143 resistant warts. J Am Acad Dermatol 1988; 18:1313-6.
16. Naples S, Brodell R T. Verruca Vulgaris: Treatment with natural interferon alpha using a needleless injector. Arch Dermatol 1993; 129:698-700.
17. Brodell R T, Bredle D L. The treatment of palmar and plantar warts using natural interferon and a needleless injector. Dermatol Surg 1995; 21:213-18.
18. Johansson E, Forstrom L. Dinitrochlorbenzene treatment of viral warts: A 5-year follow-up study. Acta Derm Venereol (Stockh) 1984; 64:529-533.
19. Naylor M F, Neldner K H, Yarbrough G K, Rosio T J, Iriondo M, Yeary J. Contact immunotherapy of resistant warts. J Am Acad Dermatol 1988; 19:679-83.
20. Watts D H, Koutsky L A, Holmes K K, Goldman D, Kuypers J, Kivat N H, Galloway D A. Low risk of perinatal transmission of human papillomavirus: results from a prospective cohort study. Am I Obstet Gynecol 1998; 365-73.
21. Swinehart J M, Skinner R B, McCarty J M, Miller B H, Tyring S K, Korey A, Orenberg E K. Development of intralesional therapy with fluorouracil/adrenaline injectable gel for management of condyloma acuminata: two phase II clinical studies. Genitourin Med 1997; 73:481-487.
22. De Villiers E M. Laboratory techniques in the investigation of human papillomavirus infection. Genitourin Med 1992; 68:50-54.
23. Wright T. Genital warts: their etiology and treatment. Nursing Times 1998; 94(7):52-54.
24. Wieland U, Pfister H. Molecular diagnosis of persistent human papillomavirus infections. Intervirology 1996; 39:145-157.
25. Fuchs P G, Pfister H. Transcription of papillomavirus genomes. Intervirology 1994; 37:159-167.
26. DeVilliers E M. Papillomavirus and HPV typing. Clinics in Dermatology 1997; 15(2): 199-206.
27. Pfister H. Human papillomavirus and skin cancer. Seminars in Cancer Biology. 1992; 3(5):263-271.
28. Zur Hausen H. ed Current Topics in Microbiology and Immunology 1994; 186:1-253.
29. Majewski S, Jablonska S. Immunology of HPV infection and HPV associated tumors. Int J Dermatol 1998; 37:81-95.
30. Pfister H, Schegget J T. Role of HPV in epithelial premalignant and malignant tumors. Clinics in Dermatology 1997; 15:335-347.
31. DeVilliers E M. Human papillomavirus infections in skin cancers. Biomed & Pharmacother 1998; 52:26-33.
32. Lutzner M A. The human papillomaviruses: a review. Arch Dermatol 1983; 119:631-634.
33. Laurent R, Kienzier J. Epidemiology of HPV infections. Clinics in Dermatology 1985; 3(4):64-69.
34. Burns D A 'Warts and all'—the history and folklore of warts: a review. Journal of the Royal Society of Medicine 1992; 85(1):37-40.
35. Routh H B, Bhowmik K R, Parish L C. Myths, fables and even truths about warts and human papillomavirus. Clinics in Dermatology 1997; 15:305-307.
36. Kilkenny M, Merlin K, Young, Marks R. The prevalence of common skin conditions in Australian school students: 1. Common, plane and plantar viral warts. Br J Dermatol 1998; 138:840-845.
37. Majewski S, Jablonska S. Human papillomavirus-associated tumors of the skin and mucosa. J Am Acad Dermatol 1997; 36:659-85.
38. Malejczyk J, Majewski S, Jablonska S. Cellular immunity in epithelial and genital HPV infections. Clinics in Dermatology 1997; 15:261-274.
39. Quan M B, Moy R L. The role of human papillomavirus in carcinoma. J Am Acad Dermatol 1991; 25:698-705.
40. Astori G, Layergne D, Benton C, Hockmayr B, Egawa K, Garbe C, de Villiers E M. Human papillomaviruses are commonly found in normal skin of immunocompetent hosts. J Invest Dermatol 1998; 110:752-755.
41. Cobb M W. Human papillomavirus infection. J Am Acad Dermatol 1990; 22:547-566.
42. Zabawski E J, Cockerell C J. Topical and intralesional cidofovir: a review of pharmacology and therapeutic effects. J Am Acad Dermatol 1998; 39:741-45.
43. DeMott K, Zoler M. Drug Update: treatment of genital warts. Skin & Allergy News 1999; 1:31.
44. Israel R M. Treatment of warts by vaccination. Arch Dermatol 1969; 100:222-23.
45. Young R, Jolley D, Marks R. Comparison of the use of standard diagnostic criteria and intuitive clinical diagnosis in the diagnosis of common viral warts (verrucae vulgaris). Arch Dermatol 1998; 134:1586-1589.
46. Feldman S R, Fleisher A B, Williford P M, Jorizzo J L. Destructive procedures are the standard of care for treatment of actinic keratosis. J Am Acad Dermatol 1999; 40:43-7.
47. Allen A L, Siegfried E C. The natural history of condyloma in children. J Am Acad Dermatol 1998; 39:951-5.
48. Hurwitz S. Anogenital warts and sexual abuse in children: a perspective. Fitzpatrick's Journal of Clinical Dermatology March/April 1994:38-39.
49. Obalek S, Jablonska S, Favre M, Walczak L, Orth G. Condyloma acuminata in children: frequent association with human papillomaviruses responsible for epithelial warts. J Am Acad Dermatol 1990; 23:205-13.
50. Chuang T Y. Condyloma acurninata (genital warts): An epidemiologic view. J Am Acad Dermatol 1987; 16:376-84.
51. Androphy E J, Beutner K, Olbright S. Human Papillomavirus infection. In: Arndt K A, LeBoit P E, Robinson J K, Wintroub B U, eds. Epithelial Medicine and Surgery. Philadelphia: W B Saunders Co, 1996:1100-1122.
52. Chopra K F, Tyring S K. The impact of the human immunodeficiency virus on the human papillomavirus epidemic. Arch Dermatol 1997; 133:629-33.
53. Edwards L, Ferenczy A, Eron L, Baker D, Owens M L, Fox T L, Hougham A J, Schmitt K A, et al. Self-administered topical 5% imiquimod cream for external anogenital warts. Arch Dermatol 1998; 134:25-30.
54. Tyring S, Edwards L, Cherry L K, Ramsdell W M, Kotner S, Greenberg M D, Vance C, Barnum G, Dromgoole S H, Killey F P. Safety and efficacy of 0.5% podofilox gel in the treatment of anogenital warts. Arch Dermatol 1998; 134:33-38.

55. Bunney M H, Nolan M W, Williams D A. An assessment of methods of treating viral warts by comparative treatment trials based on a standard design. Br J Dermatol 1976; 94:667-79.
56. Donohue M. STD prevention efforts make uneven progress. Skin & Allergy News February 1999:46.
57. Goldman E L. Topicals for anogenital warts not definitive treatment. Skin & Allergy News. February 1999:38-39.
58. Rest E B, Horn T D. Immunophenotypic analysis of benign and malignant epithelial lymphoid infitrates. Clinic Dermatol 1991:9:261-272.
59. Horn T D, Haskell J. The lymphocytic infiltrate in acute epithelial allogenic graft-versus-host reactions lacks evidence for phenotypic restriction in donor-derived cells. J Cutan Pathology 1998:210-214.
60. Chan L S, Vanderlugt C J, Hashimoto T, Nishikawa T, Zone J J, Black M M, Wojnarowska F, et al. Epitope Spreading: Lessons from autoimmune skin disease. J Invest Dermatol 1998; 110:103-109.
61. Sitz K V, Birx D L. Lymphocyte proliferation assay. In Michael N L, Kim J H, ed: Methods in molecular medicine, Vol XX: HIV Protocols, Totowa, N.J., 1999, Humana Press Inc.
62. Malling H J, Abreu-Nogueira J, Alvarez-Cuesta E, Bjorksten S, Bousquet J, Caillot D, Canonica G W, et al. Local immunotherapy. Allergy 1998; 53(10):933-44.
63. Reece D E. New advances in multiple myeloma. Current opinion in Hematology. 1998:5(6):4604.
64. Apperley J F, Dazzi F, Craddock C, Goldman J M. Immunotherapy for chronic myeloid leukemia. Hematology & Cell Therapy 1998:40(5):229-32.
65. Del Giudice G, Pizza M, Rappuoli R. Molecular basis of vaccination. Molecular Aspects of Medicine 1998:19(1): 1-70.
66. Bhan R, Pisharodi L R, Gudlaugsson E, Bedrossian C. Cytological, histological, and clinical correlations in intravesical Bacillus-Calmette-Guerin immunotherapy. Annals of Diagnostic Pathology 1998; 2(1):55-60.

What is claimed is:

1. A pharmaceutical composition comprising at least two antigens and a pharmaceutically acceptable carrier, wherein each of said antigens induces or is capable of inducing a cutaneous delayed type hypersensitivity response in a mammalian subject; and
   the composition is capable of treating a benign epithelial tumor caused by a papilloma virus in a mammalian subject;
   wherein the first of the at least two antigens is selected from the group consisting of a candida antigen, a trichophyton antigen and a mumps antigen, and the second of the at least two antigens is selected from the group consisting of a candida antigen, a trichophyton antigen, and a mumps antigen wherein the second and first antigens are not the same;
   and the at least two antigens comprise a candida antigen and a trichophyton antigen, or a candida antigen and a mumps antigen, or a trichophyton antigen and a mumps antigen.
2. The pharmaceutical composition of claim 1 wherein the composition is capable of treating a benign epithelial tumor caused by a human papilloma virus in a human subject.
3. The pharmaceutical composition of claim 1, wherein said benign epithelial tumor is a verruca, a condyloma, bowenoid papulosis, a laryngeal papilloma, or a epidermodysplasia verruciformis.
4. The pharmaceutical composition of claim 3, wherein said verruca is verruca vulgaris, verruca plantaris, verruca palmeris or verruca plana.
5. The pharmaceutical composition of claim 1, wherein said antigens are a combination of a candida antigen, a trichophyton antigen, and a mumps antigen.
6. The pharmaceutical composition of claim 1, further comprising at least one cytokine or colony stimulating factor.
7. The pharmaceutical composition of claim 6, wherein said colony stimulating factor is granulocyte macrophage colony stimulating factor and said cytokine is interferon-$\alpha$, interferon-$\beta$, interferon-$\gamma$, interleukin-2 or interleukin-12.
8. A kit comprising at least one container, a hypodermic needle or a high pressure injection device, and the pharmaceutical composition of claim 1.
9. The kit of claim 8, wherein the pharmaceutical composition comprises at least one cytokine or colony stimulating factor.
10. A pharmaceutical composition for treating an epithelial tumor in a subject comprising at least one antigen, at least one cytokine or colony stimulating factor and a pharmaceutically acceptable carrier, wherein said antigen induces or is capable of inducing a cutaneous delayed type hypersensitivity response in the subject;
    wherein the composition is capable of treating a benign epthielial tumor caused by a papilloma virus in a mammalian subject.
11. The pharmaceutical composition of claim 10, where said virus is a human papilloma virus.
12. The pharmaceutical composition of claim 10, wherein said antigen is selected from the group consisting of a viral antigen, a fungal antigen, a bacterial antigen, and a combination thereof.
13. The pharmaceutical composition of claim 12, wherein said antigen is selected from the group consisting of a candida antigen, a trichophyton antigen, a mumps antigen, and a combination thereof.
14. The pharmaceutical composition of claim 13, wherein said antigen is a combination of a candida antigen, a trichophyton antigen, and a mumps antigen.
15. The pharmaceutical composition of claim 10, wherein said colony stimulating factor is granulocyte macrophage colony stimulating factor and said cytokine is interferon-$\alpha$, interferon-$\beta$, interferon-$\gamma$, interleukin-2 or interleukin-12.
16. A kit comprising at least one container comprising the pharmaceutical composition of claim 10.
17. The kit of claim 16 further comprising a hypodermic meedle or a high pressure injection device.
18. The pharmaceutical composition of claim 1, wherein said candida antigen is an allergenic *Candida albicans* extract, said mumps antigen is an allergenic mumps extract and said trichophyton antigen is an allergenic trichophyton extract.
19. The pharmaceutical composition of claim 1, wherein said candida antigen is an allergenic *Candida albicans* extract, said mumps antigen is an allergenic mumps extract, and said trichophyton antigen is an allergenic trichophyton extract.
20. The composition of claim 1 wherein the composition comprises an allergenic *Candida albicans* extract.
21. The composition of claim 20 wherein the *Candida albicans* extract is a *Candida albicans* skin test antigen.

22. The composition of claim 1 wherein the composition comprises an allergenic mumps extract.

23. The composition of claim 22 wherein the mumps extract is a mumps skin test antigen.

24. The composition of claim 1 wherein the composition comprises an allergenic trichophyton extract.

25. The pharmaceutical composition of claim 1, wherein said pharmaceutical composition does not contain an immunogenic additive other than said antigens.

* * * * *